US005110991A

United States Patent [19]

Champion et al.

[11] Patent Number: 5,110,991

[45] Date of Patent: May 5, 1992

[54] HETEROGENEOUS CATALYST FOR ALKOXYLATION OF ALCOHOLS

[75] Inventors: Donald H. Champion, Pflugerville; George P. Speranza, Austin, both of Tex.

[73] Assignee: Texaco Chemical Company, White Plains, N.Y.

[21] Appl. No.: 677,934

[22] Filed: Apr. 1, 1991

[51] Int. Cl.[5] .................... C07C 43/18

[52] U.S. Cl. .................... 568/618; 568/608; 568/609; 568/620

[58] Field of Search .................... 568/618, 620, 608, 609

[56] References Cited

U.S. PATENT DOCUMENTS 4,721,816 1/1988 Edwards .................... 568/620

FOREIGN PATENT DOCUMENTS 0469332 7/1937 United Kingdom .................... 568/618

OTHER PUBLICATIONS

Kriomed, "Some Aspects of the Oxyethelation of Polyols," Kriobiol. Kriomed, 3, 1977, pp. 76–79.

*Primary Examiner*—Marianne Cintins
*Assistant Examiner*—Jessica H. Nguyen
*Attorney, Agent, or Firm*—Jack H. Park; Kenneth R. Priem; Cynthia L. Kendrick

[57] ABSTRACT

Disclosed is a novel method for alkoxylation alcohols by reacting the alcohols with epoxides over a heterogeneous catalyst comprising a fluoride of an element of Group I of the Periodic Table on an oxide of Group IIA or Group IIIA of the Periodic Table.

14 Claims, No Drawings

HETEROGENEOUS CATALYST FOR ALKOXYLATION OF ALCOHOLS

FIELD OF THE INVENTION

This invention relates to an improved method for preparation of polyether alcohols. More particularly, this invention relates to a method for the alkoxylation of alcohols with epoxides by passing the reactants over a heterogeneous catalyst comprising a fluoride of Group I of the Periodic Table on an oxide of Groups IIA or IIIA of the Periodic Table.

This catalyst is advantageous in that it is much easier to remove than conventional basic catalysts, such as potassium hydroxide.

BACKGROUND OF THE INVENTION

The preparation of polyols from epoxides is well-known. There is a review of catalysts generally employed for the preparation of polyols from epoxides in "Organic Polymer Chemistry", 2nd ed. Chapman and Hall, New York: 1988, pp. 182–186. The catalysts are usually alkali metal hydroxides, alkaline earth carbonates and oxides, aluminum and zinc alkyls and alkoxides. It is generally thought that polymerization occurs through a coordinated anionic mechanism, in which the ethylene oxide is coordinated to the initiator through an unshared electron pair on the oxirane oxygen atom.

A recent U.S. Pat. No. 4,894,485, to Behler et al., gives a short summary of fatty alcohol alkoxylation catalysts, including calcium and strontium hydroxides, alkoxides and phenoxides, calcium alkoxides and barium hydroxides and basic magnesium compounds. Others include magnesium and calcium fatty acid salts. This patent discloses the use of alkaline earth metal salts of ether carboxylic acids as catalysts for the ethoxylation or propoxylation of organic compounds containing active H atoms.

U.S. Pat. No. 4,341,905 to Strege describes the hydroxyalkylation of phenols and ethylene carbonates over alkalai metal halides to produce (aryloxy)ethanols. Strege describes an improvement wherein the reaction is conducted without addition of strong acid or base using as the catalyst an inorganic halide salt.

With most of the catalysts used in the art to alkoxylate alcohols, removal of the catalyst is difficult. It would be a distinct advance in the art if an alkoxylation catalyst were available which allowed for good yield of polyols and at the same time allowed for an efficient means of removal of the catalyst from the reactor.

KF on alumina catalysts have been used for aldol condensations and Michael additions of nitroalkanes to $\alpha,\beta$-unsaturated carbonyl compounds. The preparation of these catalysts is described by Bergbreiter, D. E. in *J. Org. Chem.*, 1987, 52, 1601–1603.

There is nothing in the art which would indicate the usefulness of a supported potassium or cesium fluoride supported on an alkaline earth metal oxide for alkoxylation of long-chain alcohols. It has now been discovered that a supported heterogeneous catalyst comprising a fluoride of Group I and an oxide of Groups IIA or IIIA can be employed for the preparation of polyether alcohols by alkoxylation and is much easier to remove from the reactor than conventional catalysts. Polyether alcohols find a wide variety of uses, including in polyurethanes and surfactants.

SUMMARY OF THE INVENTION

In accordance with the foregoing, the present invention provides a method of ethoxylation or propoxylation of alcohols using a heterogeneous catalyst comprising a fluoride of Group I of the Periodic Table supported on an oxide of Groups IIA or IIIA of the Periodic Table at a temperature of from about 25° C. to about 200° C. and a pressure of atmospheric to about 1500 psig.

DETAILED DESCRIPTION OF THE INVENTION

This invention describes a method for alkoxylating alcohols and alkylene oxides over a supported catalyst in the preparation of polyether alcohols.

The catalyst appears to be useful in the alkoxylation of primarily longer chain alcohols. Alcohols which can be used include long-chain fatty alcohols and phenols. The general formula can be represented by ROH where R is selected from the group consisting of linear or branched $C_1$–$C_{22}$ alkyl, linear or branched $C_3$–$C_{22}$ alkenyl, phenyl and alkylphenyl containing 1 to 3 $C_1$–$C_{15}$ alkyl radicals, benzyl and phenylether alcohols. Preferred alcohols include those having about 8–20 carbons. For example, nonylphenol as well as certain alcohols containing 10–20 carbons were demonstrated to react over the catalysts to form the desired polyols.

Suitable epoxides which are reacted with the alcohols over the catalysts are generally alkylene oxides containing 2 to 4 carbon atoms. Suitable epoxides include 1,2-butylene oxide, propylene oxide and ethylene oxide. Reaction of the oxides to the initiator is exothermic and can be controlled by adjusting the amount of oxide introduced to the reactor. The examples demonstrate the usefulness of propylene oxide and ethylene oxide.

The catalyst employed for the alkoxylation of alcohols comprise a fluoride of Group I of the Periodic Table supported on an oxide of Groups IIA or IIIA of the Periodic Table.

The fluoride of Group I can be a compound containing, for example, cesium or potassium and fluorine. The Group IIA or Group IIIA oxide may include alumina, magnesium oxide, calcium oxide or barium oxide. Suitable heterogeneous supported catalysts for fixed bed operation can be obtained by treating the oxides prepared in a desired size of extrudates, tablets, spheres, etc. with an aqueous solution of Group I fluoride followed by drying in the manner demonstrated in the examples. Particularly good results were observed using potassium fluoride on alumina and potassium fluoride on magnesium oxide.

The quantity of a fluoride of a Group I element deposited on a support may vary. The reaction proceeds when employing as little as about 10% to 50% of Group I fluoride together with about 50 to 90 wt. % Groups IIA or IIIA oxide basis the total weight of the catalyst.

The temperature range which can be usefully employed is variable depending upon other experimental factors, including the pressure and choice of particular species of catalyst among other things. The range of operability is from about 25°–200° C. A narrow range of 70°–150° C. is preferred. The examples demonstrate that the most preferred temperature is 100° to 140° C.

Pressures of atmospheric to 1000 psig can be used. In most instances very mild pressures of about 50–200 psig are sufficient.

The novel catalyst can typically be introduced into an autoclave initially and the reactants can be continuously or intermittently introduced into such a zone during the course of the reaction. Operating conditions can be adjusted to optimize formation of the desired polyether polyol products. The products are recovered by filtration.

The products have been identified by NMR, and liquid chromatography in most cases. The meq/g of acetylatables was identified by potentiometric titration. For instance, in Example 1 the product was found to contain about 7.27 meq/g acetylatables (average) implying an average molecular weight of 420 g/mole.

Various embodiments of the process of this invention are demonstrated in the following examples which are only intended to be illustrative and are not intended to limit the invention in any way.

EXAMPLE 1

To a 300 ml stirred autoclave was charged 50 g (0.54 mol) glycerin and 1.0 g 40% potassium fluoride on alumina catalyst. After purging twice with nitrogen, 25 g of propylene oxide was added. The mixture was heated to 136° C. as the pressure rose to 118 psig and began to drop to 80 psig over 6 minutes. Propylene oxide addition was continued in portions over 2½ hours at 130°-140° C. and 15-90 psig. A total of 165 g (2.84 mol) propylene oxide was added. The autoclave contents were digested for 1 hour at 130°-135° C. To the product was added 1.0 g oxalic acid dihydrate and the mixture was stripped at 100°-105° C. and 0.6 torr for 1 hour and filtered to give a product with 7.27 meq/g acetylatables (average) implying an average molecular weight of 420 g/mole.

EXAMPLE 2

To a solution of 5.0 g potassium fluoride dihydrate in 20 g water was added 15.0 g magnesium oxide. An additional 20 g of water was added and the resulting slurry transferred to a flask with the aid of water. Water was removed by rotary evaporation followed by treatment at 100° C. and 0.25 torr for 7 hours in a vacuum desiccator to give a 17% KF/MgO catalyst.

The reaction of Example 1 was repeated substituting 1.0 g of the KF/MgO catalyst for the KF on alumina. A product with 8.17 meq/g acetylatables (average) was obtained.

EXAMPLE 3

In a manner similar to Example 1, 73.5 g (0.333 mol) nonylphenol was ethoxylated over 5.0 g 40% KF on alumina at about 100° C. A total of 147 g of ethylene oxide (3.34 mol) were charged. The product was found to contain 9 wt. % PEG by HPLC and 1.77 meq/g acetylatables. The cloud point of a 1% aqueous solution was 50° C.

EXAMPLE 4

The reaction of Example 3 was repeated except that the KF on alumina was replaced by the KF/MgO catalyst of Example 2 and the nonylphenol and catalyst charge was stripped in the autoclave at 100° C. under vacuum for 1 hour before the ethylene oxide addition was begun. This resulted in a product containing 1.7% PEG and 1.58 meq/g acetylatables. A 1% aqueous solution gave a cloud point of 66° C.

EXAMPLE 5

Ethoxylation of 78.8 g (0.40 mol) $C_{12-16}$ alcohol (EPAL® 1214) with 123 g (2.79 mol) ethylene oxide over 5.0 g 40% KF on alumina at 120°-125° C. in a manner similar to Example 1 gave a product containing 8.3% PEG and 2.30 meq/g acetylatables. A 1% aqueous solution gave a cloud point of 40° C.

EXAMPLE 6

To a 300 ml stirred autoclave was charged 65 g (0.25 mol) N,N'-bis(2-hydroxyethyl)-N,N'-bi-t-butylethylene-diamine and 5.0 g 40% KF on alumina catalyst. Ethoxylation was carried out similar to the above examples at 106°-108° C. A total of 110 g (10.0 moles) ethylene oxide was charged to the reactor. The product was treated with 0.15 g DBPC and filtered before stripping at 55°-60° C. and 0.5 to 0.7 torr for 1½ hours to give a product with 3. meq/g acetylatables.

What is claimed is:

1. A method for producing polyether alcohols which comprises reacting an alcohol of the formula ROH where R is $C_1$-$C_{22}$ alkyl and an epoxide over a heterogeneous catalyst which consists of a fluoride of Group I of the Periodic Table supported on alumina at a temperature of about 70-150° and a pressure of atmospheric to 1500 psig.

2. The method of claim 1 wherein the alkoxylation catalyst comprises 15-45% by total weight of the catalyst potassium fluoride on an alumina support.

3. The method of claim 1 where the alcohol contains 8-20 carbons.

4. The method of claim 1 where the alcohol is nonylphenol.

5. The method of claim 1 where the alcohol is a $C_{12}$-$C_{16}$ alcohol.

6. The method of claim 1 where the epoxide is ethylene oxide.

7. The method of claim 1 where the epoxide is propylene oxide.

8. The method of claim 1 wherein the catalyst, alcohol and a portion of the epoxide are heated in an autoclave and then epoxide is added in portions to control the reaction.

9. The method of claim 1 wherein a mixture of alcohol and epoxide are passed continuously over a fixed bed of the supported catalyst.

10. The method of claim 1 wherein the fluoride of Group I of the Periodic Table is selected from the group consisting of potassium fluoride and cesium fluoride.

11. The method of claim 1 wherein the fluoride of Group I of the Periodic Table is selected from the group consisting of potassium fluoride and potassium fluoride hydrate.

12. A method for ethoxylating glycerin by reacting glycerin with propylene oxide in the presence of a catalyst comprising about 15-45% by total weight of the catalyst KF on alumina and heating to about 125°-140° C. at pressures between about 50 and 120 psig.

13. A method for alkoxylating nonylphenol by reacting nonylphenol with ethylene oxide in the presence of a catalyst consisting of about 15-45% by total weight of the catalyst KF on alumina at a temperature of about 100°-140° C. and pressures between about 50 and 120 psig.

14. A method for alkoxylating nonylphenol by reacting nonylphenol with ethylene oxide in the presence of a catalyst consisting of about 15-25% by total weight of the catalyst potassium fluoride on magnesium oxide at a temperature of about 100° to 150° C. and pressure of between 50 and 120 psig.

* * * * *